United States Patent
Shelton, IV et al.

(10) Patent No.: US 10,238,388 B2
(45) Date of Patent: Mar. 26, 2019

(54) SURGICAL STAPLER BUTTRESS ASSEMBLY WITH HUMIDITY TOLERANT ADHESIVE

(71) Applicant: Ethicon Endo-Surgery, LLC, Guaynabo, PR (US)

(72) Inventors: Frederick E. Shelton, IV, Hillsboro, OH (US); Michael J. Vendely, Lebanon, OH (US); Prudence A. Turner, Independence, KY (US); Jack Donners, Somerville, NJ (US); Rao S. Bezwada, Whitehouse Station, NJ (US); Aidan Craigwood, Cambridge (GB); Caroline Hagerman, Cambridge (GB); Ashley Easter, Cambridge (GB); Kathrin Holtzmann, Cambridge (GB)

(73) Assignee: Ethicon LLC, Guaynabo, PR (US)

( * ) Notice: Subject to any disclaimer, the term of this patent is extended or adjusted under 35 U.S.C. 154(b) by 399 days.

(21) Appl. No.: 14/926,045

(22) Filed: Oct. 29, 2015

(65) Prior Publication Data

US 2017/0119379 A1 May 4, 2017

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 17/07292* (2013.01);
(Continued)

(58) Field of Classification Search
CPC ..... A61B 17/068; A61L 31/06; A61L 31/148; A61F 2/02; A61K 9/70; B32B 5/12; C08L 69/00
(Continued)

(56) References Cited

U.S. PATENT DOCUMENTS 4,359,510 A * 11/1982 Taskier .............. B01D 67/0088
429/144
4,374,957 A * 2/1983 Quirk .................... C08F 297/04
525/314
(Continued)

FOREIGN PATENT DOCUMENTS

EP          1 064 883 A1       1/2001

OTHER PUBLICATIONS

U.S. Appl. No. 62/209,041, filed Aug. 24, 2015.
(Continued)

*Primary Examiner* — Nathaniel Chukwurah
(74) *Attorney, Agent, or Firm* — Frost Brown Todd LLC

(57) ABSTRACT

A buttress assembly is configured to temporarily adhere to a wet surgical stapler end effector. The buttress assembly includes a buttress body and a humidity tolerant adhesive. The adhesive includes a bioabsorbable polymer having a block configuration selected from the group consisting of A-B-A and A-B-C. The A block is a bioabsorbable homopolymer characterized by a glass transition temperature of at least about 0° C., a crystallinity as measured by X-ray diffraction of at least about 30%, and a melting temperature of at least about 50° C. The B block is a bioabsorbable homopolymer or co-polymer that is characterized by a glass transition temperature of at least about −40° C., a crystallinity as measured by X-ray diffraction of at most about 25%, and 2 a molecular weight of from about 20 to about 80 kDa. The C block is a bioabsorbable hydrophilic homopolymer or co-polymer that is miscible with water at 37° C.

20 Claims, 9 Drawing Sheets

(51) Int. Cl.
*A61L 24/00* (2006.01)
*A61L 24/04* (2006.01)
*C08G 63/664* (2006.01)
*C09J 167/04* (2006.01)
*A61L 31/06* (2006.01)
*A61L 31/14* (2006.01)
*A61B 17/00* (2006.01)

(52) U.S. Cl.
CPC ......... *A61L 24/0042* (2013.01); *A61L 24/046* (2013.01); *A61L 31/06* (2013.01); *A61L 31/148* (2013.01); *C08G 63/664* (2013.01); *C09J 167/04* (2013.01); *A61B 2017/00004* (2013.01); *A61B 2017/00526* (2013.01); *A61B 2017/00951* (2013.01)

(58) Field of Classification Search
USPC .................... 227/175.1, 19, 179.1, 180.1
See application file for complete search history.

(56) References Cited

U.S. PATENT DOCUMENTS

| | | | |
|---|---|---|---|
| 4,438,185 A * | 3/1984 | Taskier | B01D 69/12 427/245 |
| 4,805,823 A | 2/1989 | Rothfuss | |
| 5,415,334 A | 5/1995 | Williamson et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,093,792 A * | 7/2000 | Gross | A61K 9/70 528/196 |
| 6,165,217 A * | 12/2000 | Hayes | A61L 31/06 428/36.4 |
| 6,231,565 B1 | 5/2001 | Tovey et al. | |
| 6,319,521 B1 * | 11/2001 | Randolph | A61K 9/1647 424/484 |
| 6,325,810 B1 * | 12/2001 | Hamilton | A61B 17/07207 227/175.1 |
| 6,364,888 B1 | 4/2002 | Niemeyer et al. | |
| 6,503,257 B2 | 1/2003 | Grant et al. | |
| 6,783,524 B2 | 8/2004 | Anderson et al. | |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney | |
| 7,691,098 B2 | 4/2010 | Wallace | |
| 7,721,930 B2 | 5/2010 | McKenna et al. | |
| 7,806,891 B2 | 10/2010 | Nowlin et al. | |
| 8,141,762 B2 | 3/2012 | Bedi et al. | |
| 8,210,411 B2 | 7/2012 | Yates et al. | |
| 8,371,491 B2 | 2/2013 | Huitema et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,801,735 B2 | 8/2014 | Shelton, IV et al. | |
| 8,814,025 B2 | 8/2014 | Miller et al. | |
| 8,820,605 B2 | 9/2014 | Shelton, IV | |
| 8,844,789 B2 | 9/2014 | Shelton, IV et al. | |
| 8,899,464 B2 | 12/2014 | Hueil et al. | |
| 8,998,060 B2 | 4/2015 | Bruewer et al. | |
| 9,101,359 B2 | 8/2015 | Smith et al. | |
| 9,186,142 B2 | 11/2015 | Fanelli et al. | |
| 9,198,644 B2 | 12/2015 | Balek et al. | |
| 9,211,120 B2 | 12/2015 | Scheib et al. | |
| 9,301,759 B2 | 4/2016 | Spivey et al. | |
| 9,393,018 B2 | 7/2016 | Wang et al. | |
| 9,398,911 B2 | 7/2016 | Auld | |
| 9,492,170 B2 | 11/2016 | Bear et al. | |
| 9,517,065 B2 | 12/2016 | Simms et al. | |
| 2007/0026039 A1 * | 2/2007 | Drumheller | A61L 27/18 424/424 |
| 2007/0026043 A1 * | 2/2007 | Guan | A61L 31/10 424/426 |
| 2007/0269485 A1 * | 11/2007 | Richard | A61L 27/16 424/426 |
| 2008/0169328 A1 | 7/2008 | Shelton, IV | |
| 2008/0247987 A1 * | 10/2008 | Liggins | A61K 9/0014 424/78.17 |
| 2008/0286326 A1 * | 11/2008 | Benco | A61L 27/34 424/423 |
| 2012/0241493 A1 | 9/2012 | Baxter, III et al. | |
| 2013/0062391 A1 | 3/2013 | Boudreaux et al. | |
| 2013/0068816 A1 | 3/2013 | Vasudevan et al. | |
| 2013/0075447 A1 | 3/2013 | Weisenburgh, II et al. | |
| 2013/0206813 A1 | 8/2013 | Nalagatla | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239043 A1 | 8/2014 | Simms et al. | |
| 2014/0239044 A1 | 8/2014 | Hoffman | |
| 2014/0263563 A1 | 9/2014 | Stokes et al. | |
| 2015/0272575 A1 | 10/2015 | Leimbach et al. | |
| 2015/0351754 A1 | 12/2015 | Harris et al. | |
| 2015/0351758 A1 | 12/2015 | Shelton, IV et al. | |
| 2015/0351763 A1 | 12/2015 | Shelton, IV et al. | |
| 2015/0374360 A1 | 12/2015 | Scheib et al. | |
| 2015/0374373 A1 | 12/2015 | Rector et al. | |
| 2016/0089146 A1 | 3/2016 | Harris et al. | |
| 2016/0278774 A1 | 9/2016 | Shelton, IV et al. | |

OTHER PUBLICATIONS

U.S. Appl. No. 14/827,856, filed Aug. 17, 2015.
U.S. Appl. No. 14/840,613, filed Aug. 31, 2015.
U.S. Appl. No. 14/871,071, filed Sep. 30, 2015.
U.S. Appl. No. 14/871,131, filed Sep. 30, 2015.
European Search Report and Written Opinion dated Feb. 28, 2017 for Application No. EP 16196364.0, 7 pgs.
International Search Report and Written Opinion dated Feb. 20, 2017 for Application No. PCT/US2016/058389, 9 pgs.

* cited by examiner

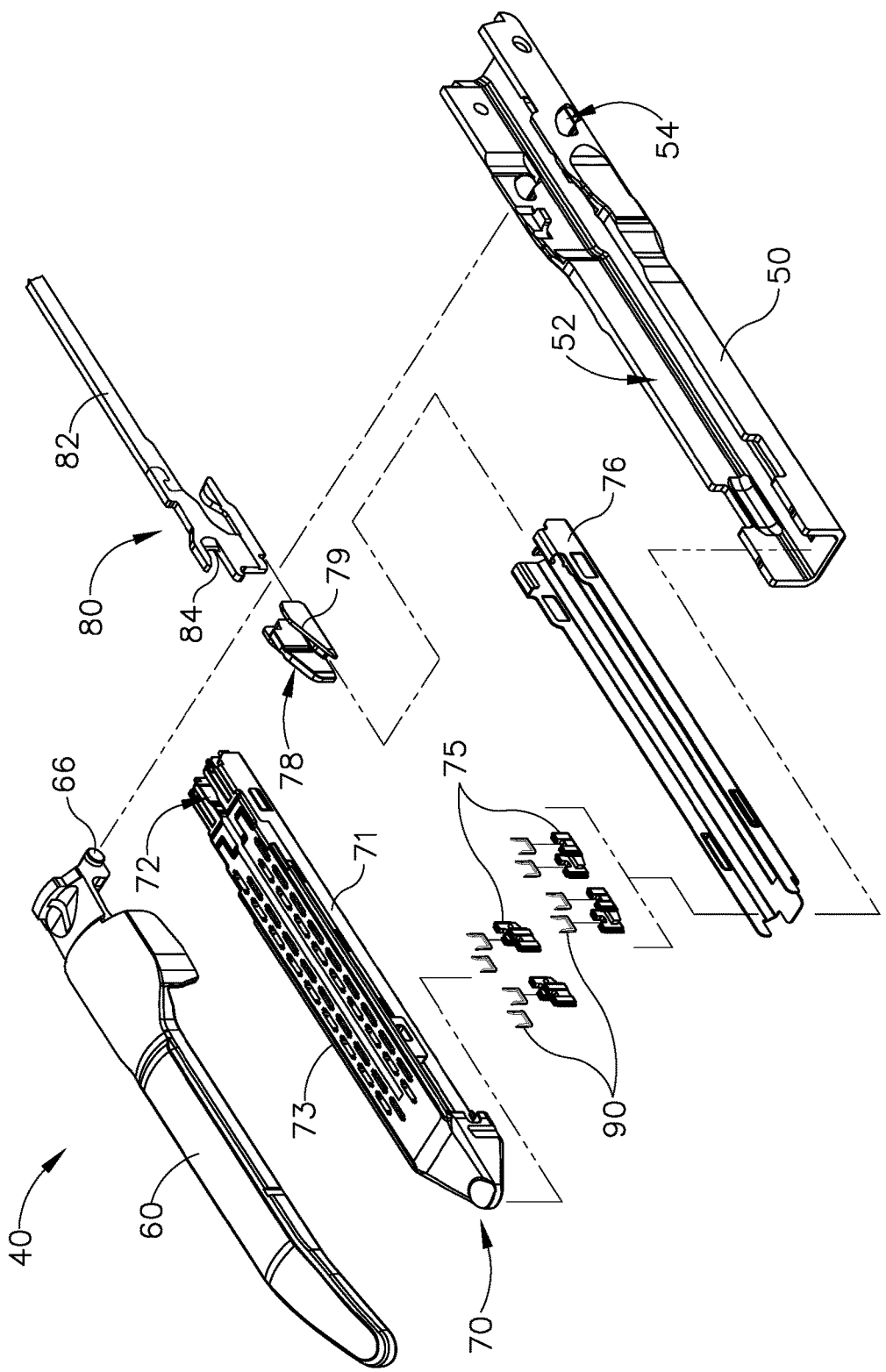

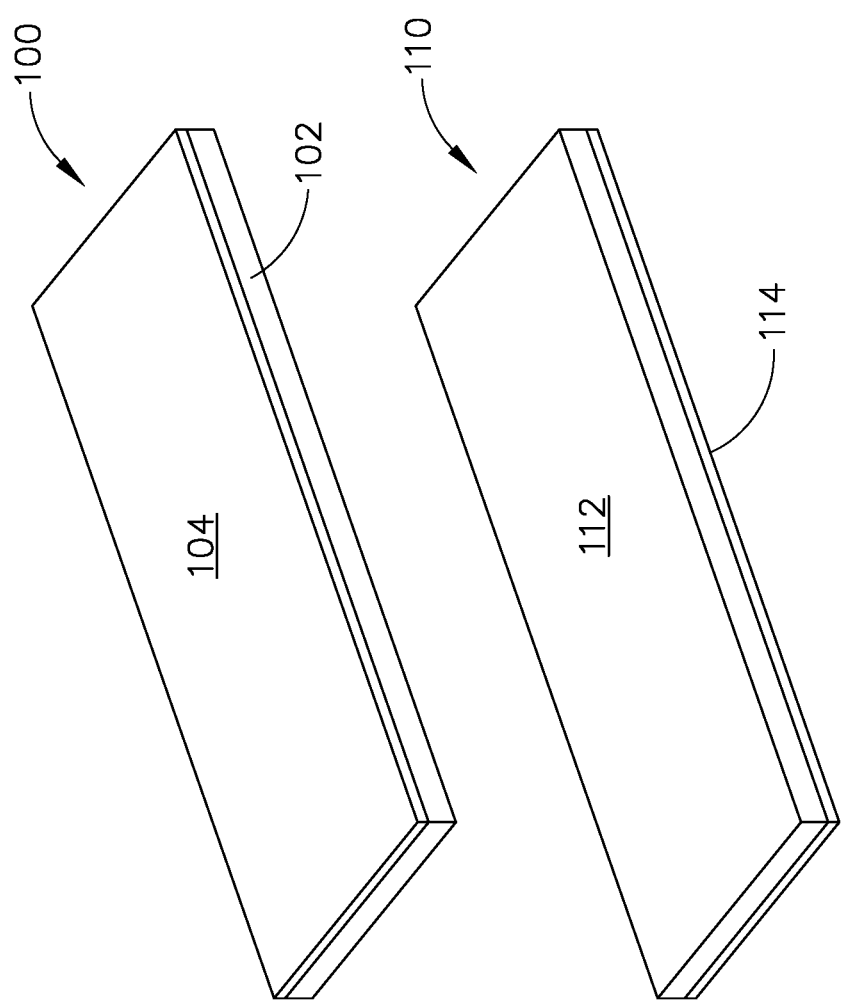

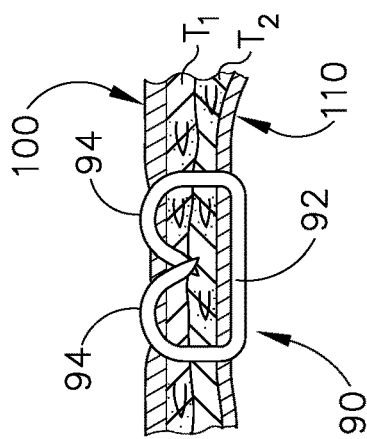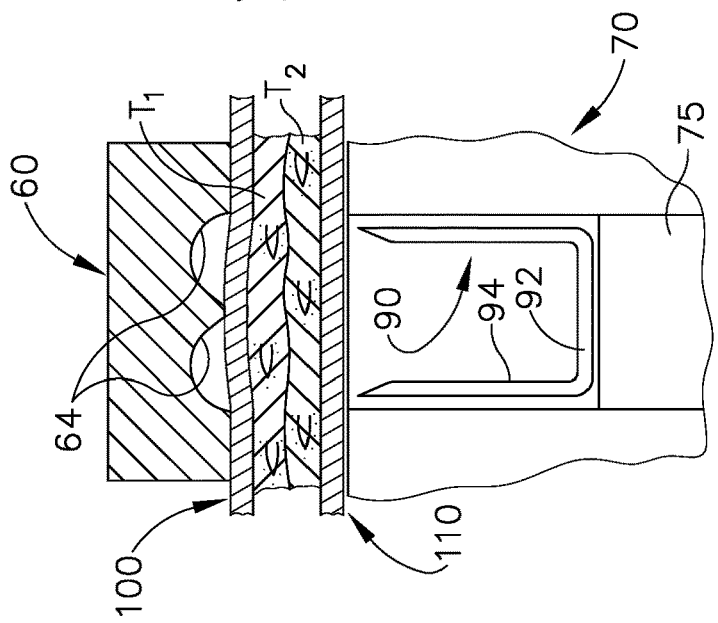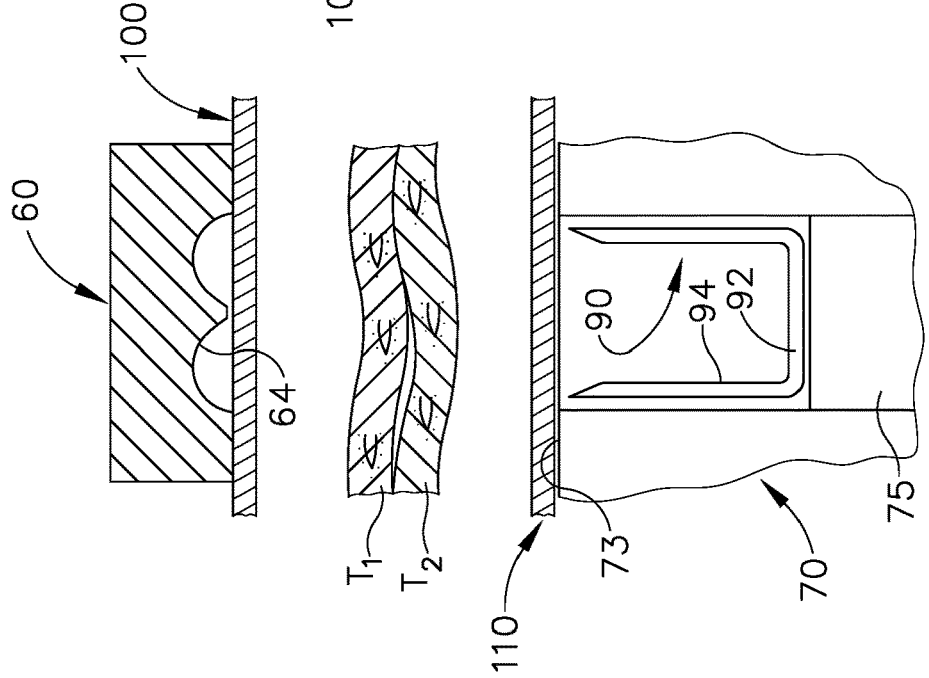

SURGICAL STAPLER BUTTRESS ASSEMBLY WITH HUMIDITY TOLERANT ADHESIVE

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014; U.S. Patent Pub. No. 2014/0239041, entitled "Lockout Feature for Movable Cutting Member of Surgical Instrument," published Aug. 28, 2014; U.S. Patent Pub. No. 2014/0239042, entitled "Integrated Tissue Positioning and Jaw Alignment Features for Surgical Stapler," published Aug. 28, 2014; U.S. Patent Pub. No. 2014/0239036, entitled "Jaw Closure Feature for End Effector of Surgical Instrument," published Aug. 28, 2014; U.S. Patent Pub. No. 2014/0239040, entitled "Surgical Instrument with Articulation Lock having a Detenting Binary Spring," published Aug. 28, 2014; U.S. Patent Pub. No. 2014/0239043, entitled "Distal Tip Features for End Effector of Surgical Instrument," published Aug. 28, 2014; U.S. Patent Pub. No. 2014/0239037, entitled "Staple Forming Features for Surgical Stapling Instrument," published Aug. 28, 2014; U.S. Patent Pub. No. 2014/0239038, entitled "Surgical Instrument with Multi-Diameter Shaft," published Aug. 28, 2014; and U.S. Patent Pub. No. 2014/0239044, entitled "Installation Features for Surgical Instrument End Effector Cartridge," published Aug. 28, 2014. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014; U.S. Pub. No. 2014/0246473, entitled "Rotary Powered Surgical Instruments with Multiple Degrees of Freedom," published Sep. 4, 2014; U.S. Pub. No. 2013/0206813, entitled "Linear Stapler," published Aug. 15, 2013; U.S. Pub. No. 2008/0169328, entitled "Buttress Material for Use with a Surgical Stapler," published Jul. 17, 2008; U.S. patent application Ser. No. 14/300,804, entitled "Woven and Fibrous Materials for Reinforcing a Staple Line," filed Jun. 10, 2014; U.S.

patent application Ser. No. 14/300,811, entitled "Devices and Methods for Sealing Staples in Tissue"; and U.S. patent application Ser. No. 14/498,070, entitled "Radically Expandable Staple Line" filed Sep. 26, 2014. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 3 depicts an exploded perspective view of the end effector of FIG. 2;

FIG. 4 depicts a perspective view of an exemplary upper buttress and an exemplary lower buttress, each of which may be applied to the end effector of FIG. 2;

FIG. 5A depicts a cross-sectional end view of a portion of the end effector of FIG. 2 with a buttress assembly formed by the buttresses of FIG. 4 applied to the end effector, with tissue positioned between the buttresses in the end effector, and with the anvil in an open position;

FIG. 5B depicts a cross-sectional end view of the combined end effector and buttress assembly of FIG. 5A, with tissue positioned between the buttresses in the end effector, and with the anvil in a closed position;

FIG. 5C depicts a cross-sectional view of a staple and the buttress assembly of FIG. 5A having been secured to the tissue by the end effector of FIG. 2;

Figure 1:
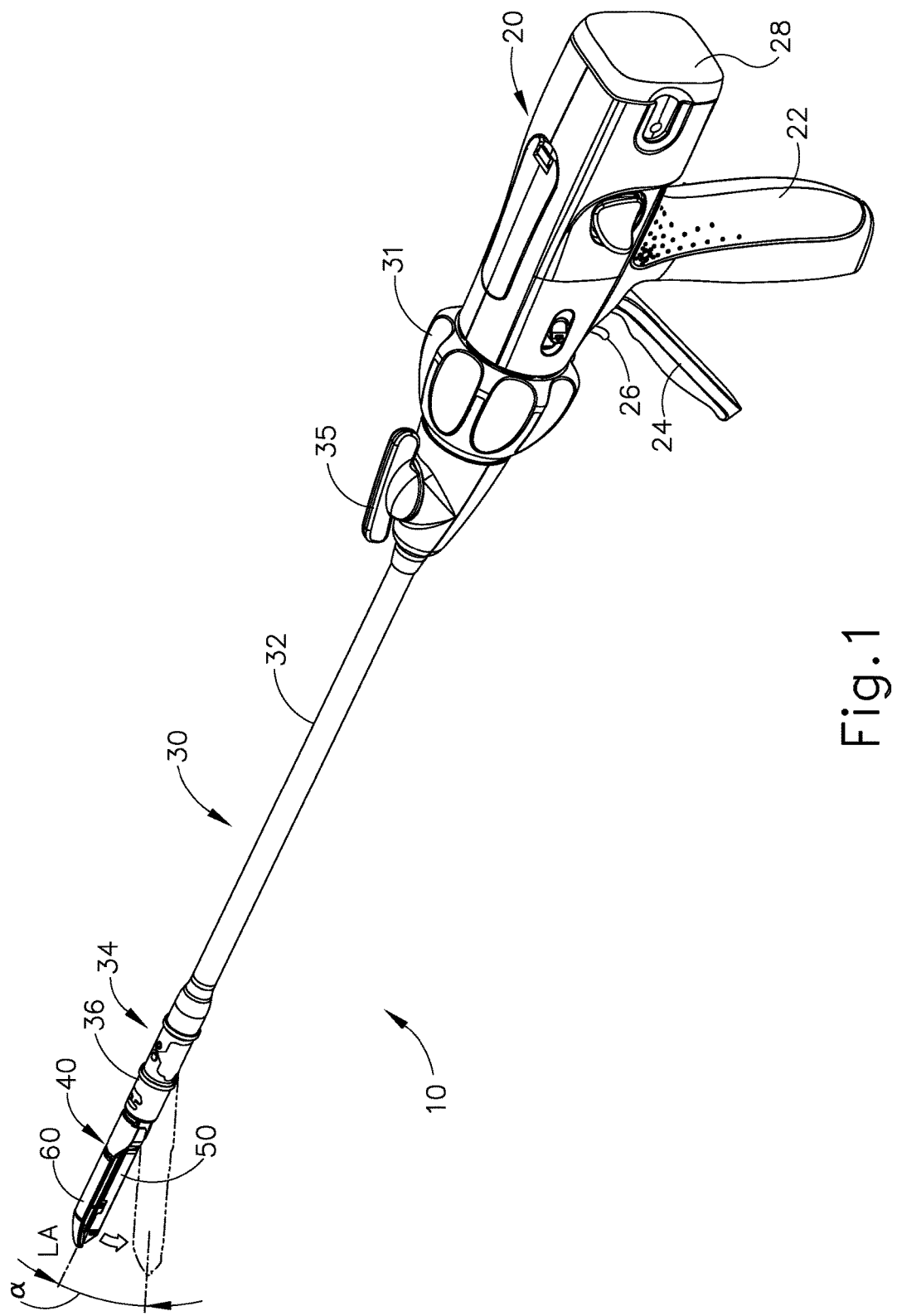
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
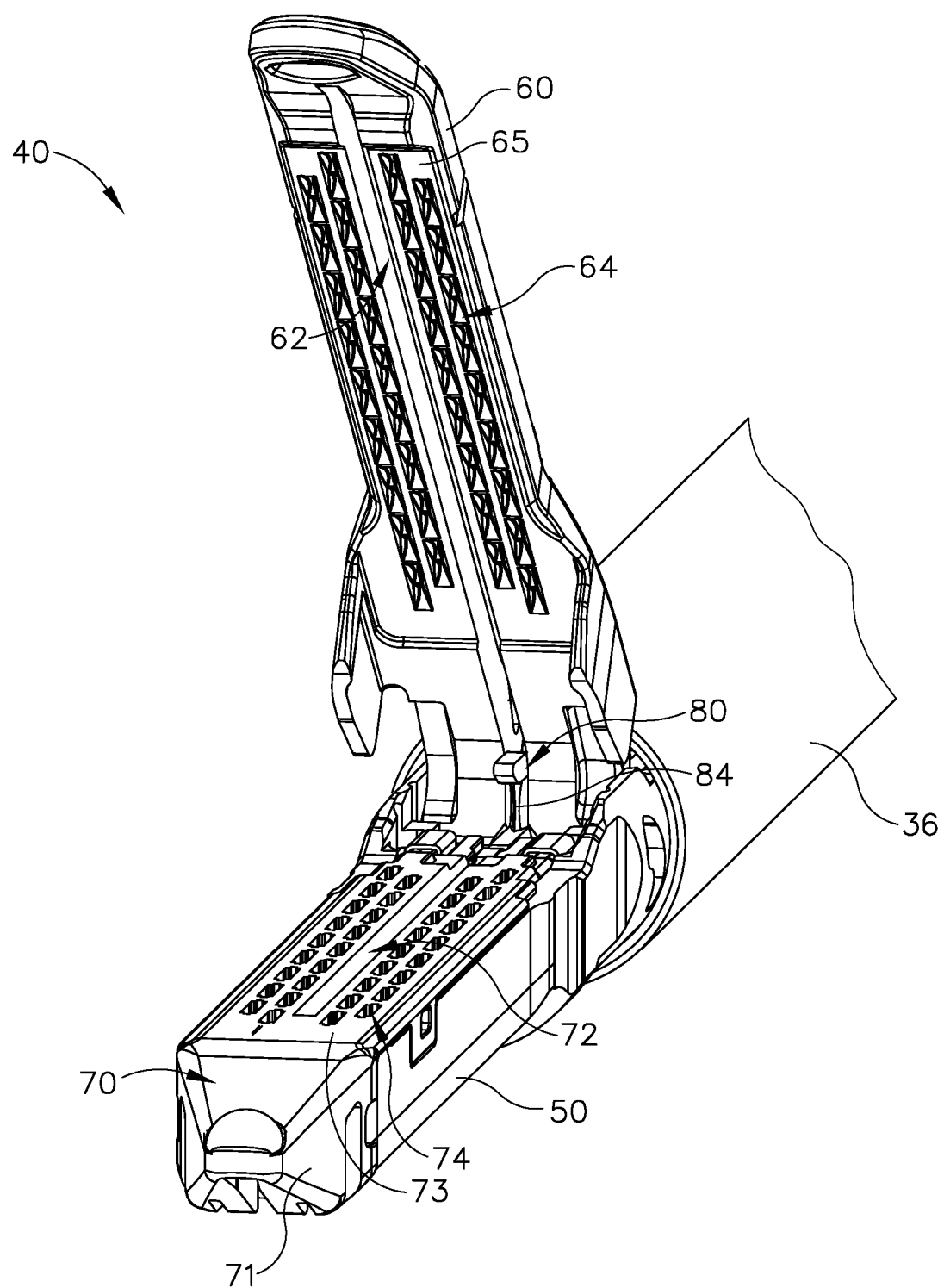
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, the disclosure of which is incorporated by reference herein; and/or U.S. patent application Ser. No. 14/314,125, entitled "Articulation Drive Features for Surgical Stapler," filed Jun. 25, 2014, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, the disclosure of which is incorporated by reference herein. Other suitable configurations for shaft assembly (30) will be apparent to those of ordinary skill in the art in view of the teachings herein.

B. Exemplary End Effector

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014; at least some of the teachings of U.S. Pub. No. 2014/0239036, entitled "Jaw Closure Feature for End Effector of Surgical Instrument," published Aug. 28, 2014; and/or at least some of the teachings of U.S. Pub. No. 2014/0239037, entitled "Staple Forming Features for Surgical Stapling Instrument," published Aug. 28, 2014, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. patent application Ser. No. 14/226,142, entitled "Surgical Instrument Comprising a Sensor System," filed Mar. 26, 2014, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress Assembly for Surgical Stapler

In some instances, it may be desirable to equip end effector (40) with a buttress material to reinforce the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress Assembly for Surgical Stapler

FIG. 4 shows an exemplary pair of buttress assemblies (100, 110) with a basic composition. Buttress assembly (100) of this example comprises a buttress body (102) and an upper adhesive layer (104). Similarly, buttress assembly (110) comprises a buttress body (112) and a lower adhesive layer (114). In the present example, each buttress body (102, 112) comprises a strong yet flexible material configured to structurally support a line of staples (90). By way of example only, each buttress body (102, 112) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (102, 112). Each buttress body (102, 112) may take any other suitable form and may be constructed of any other suitable material(s). By way of further example only, each buttress body (102, 112) may comprise one or more of the following: NEOVEIL absorbable PGA felt by Gunze Limited, of Kyoto, Japan; SEAMGUARD polyglycolic acid:trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress body (102, 112) will be apparent to those of ordinary skill in the art in view of the teachings herein.

In addition or in the alternative, each buttress body (102, 112) may comprise a material including, for example, a hemostatic agent such as fibrin to assist in coagulating blood and reduce bleeding at the severed and/or stapled surgical site along tissue (90). As another merely illustrative example, each buttress body (102, 112) may comprise other adjuncts or hemostatic agents such as thrombin may be used such that each buttress body (102, 112) may assist to coagulate blood and reduce the amount of bleeding at the surgical site. Other adjuncts or reagents that may be incorporated into each buttress body (102, 112) may further include but are not limited to medical fluid or matrix components. Merely illustrative examples of materials that may be used to form each buttress body (102, 112), as well as materials that may be otherwise incorporated into each buttress body (102, 112), are disclosed in U.S. patent application Ser. No. 14/667,842, entitled "Method of Applying a Buttress to a Surgical Stapler," filed Mar. 25, 2015, the disclosure of which is incorporated by reference herein. Alternatively, any other suitable materials may be used.

By way of further example only, each buttress body (102, 112) may be constructed in accordance with at least some of the teachings of U.S. Patent Pub. No. 2012/0241493, entitled "Tissue Thickness Compensator Comprising Controlled Release and Expansion," published Sep. 27, 2012, the disclosure of which is incorporated by reference herein; U.S. Patent Pub. No. 2013/0068816, entitled "Surgical Instrument and Buttress Material," published Mar. 21, 2013, the disclosure of which is incorporated by reference herein; U.S. Patent Pub. No. 2013/0062391, entitled "Surgical Instrument with Fluid Fillable Buttress," published Mar. 14, 2013, the disclosure of which is incorporated by reference herein; U.S. Patent Pub. No. 2013/0068820, entitled "Fibrin Pad Matrix with Suspended Heat Activated Beads of Adhesive," published Mar. 21, 2013, the disclosure of which is incorporated by reference herein; U.S. Patent Pub. No. 2013/0082086, entitled "Attachment of Surgical Staple Buttress to Cartridge," published Apr. 4, 2013, the disclosure of which is incorporated by reference herein; U.S. Patent Pub. No. 2013/0037596, entitled "Device for Applying Adjunct in Endoscopic Procedure," published Feb. 14, 2013, the disclosure of which is incorporated by reference herein; U.S. Patent Pub. No. 2013/0062393, entitled "Resistive Heated Surgical Staple Cartridge with Phase Change Sealant," published Mar. 14, 2013, the disclosure of which is incorporated by reference herein; U.S. Patent Pub. No. 2013/0075446, entitled "Surgical Staple Assembly with Hemostatic Feature," published Mar. 28, 2013, the disclosure of which is incorporated by reference herein; U.S. Patent Pub. No. 2013/0062394, entitled "Surgical Staple Cartridge with Self-Dispensing Staple Buttress," published Mar. 14, 2013, the disclosure of which is incorporated by reference herein; U.S. Patent Pub. No. 2013/0075445, entitled "Anvil Cartridge for Surgical Fastening Device," published Mar. 28, 2013, the disclosure of which is incorporated by reference herein; U.S. Patent Pub. No. 2013/0075447, entitled "Adjunct Therapy for Applying Hemostatic Agent," published Mar. 28, 2013, the disclosure of which is incorporated by reference herein; U.S. Patent Pub. No. 2013/0256367, entitled "Tissue Thickness Compensator Comprising a Plurality of Medicaments," published Oct. 3, 2013, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, the disclosure of which is incorporated by reference herein; U.S. patent application Ser. No. 14/827,856, entitled "Implantable Layers for a Surgical Instrument," filed Aug. 17, 2015, the disclosure of which is incorporated by reference herein; U.S. patent application Ser. No. 14/840,613, entitled "Drug Eluting Adjuncts and Methods of Using Drug Eluting Adjuncts," filed Aug. 31, 2015, the disclosure of which is incorporated by reference herein; U.S. patent application Ser. No. 14/871,071, entitled "Compressible Adjunct with Crossing Spacer Fibers," filed Sep. 30, 2015, the disclosure of which is incorporated by reference herein; and/or U.S. patent application Ser. No. 14/871,131, entitled "Method for Applying an Implantable Layer to a Fastener Cartridge," filed Sep. 30, 2015, the disclosure of which is incorporated by reference herein.

In the present example, adhesive layer (104) is provided on buttress body (102) in order to adhere buttress body (102) to underside (65) of anvil (60). Similarly, adhesive layer (114) is provided on buttress body (112) in order to adhere buttress body (112) to deck (73) of staple cartridge (70). Adherence of the buttress body (102) to underside (65) of anvil (60) or to deck (73) of staple cartridge (70) can occur through a variety of mechanisms including but not limited to a pressure sensitive adhesive. In some versions, each adhesive layer (104, 114) comprise a pressure sensitive adhesive material. Examples of various suitable materials that may be used to form adhesive layers (104, 114) are disclosed in U.S. patent application Ser. No. 14/667,842, entitled "Method of Applying a Buttress to a Surgical Stapler," filed Mar. 25, 2015, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (104, 114) will be apparent to those of ordinary skill in the art in view of the teachings herein.

B. Exemplary Materials and Techniques for Providing Adhesion of Buttress to Surgical Stapler As noted above, a buttress assembly (100) may include a layer (104, 114) of adhesive material (or other form of adhesive material) that adheres buttress body (102, 112) to either underside (65) of anvil (60) or deck (73) of staple cartridge (70). Such an adhesive material may provide proper positioning of buttress body (102, 112) before and during actuation of end effector (40); then allow buttress body (102, 112) to separate from end effector (40) after end effector (40) has been actuated, without causing damage to buttress body (102, 112) that is substantial enough to compromise the proper subsequent functioning of buttress body (102, 112).

FIGS. 5A-5C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 5A shows layers of tissue ($T_1$, $T_2$) positioned between anvil (60) and staple cartridge (70), with anvil (60) in the open position. Buttress assembly (100) is adhered to the underside (65) of anvil (60) via adhesive layer (104); while buttress assembly (110) is adhered to deck (73) of staple cartridge (70) via adhesive layer (114). Layers of tissue ($T_1$, $T_2$) are thus interposed between buttress assemblies (100, 110). Next, trigger (24) is pivoted toward pistol grip (22) to drive closure tube (32) and closure ring (36) distally. This drives anvil (60) to the closed position as shown in FIG. 5B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated as described above, driving staple (90) through buttress assemblies (100, 110) and tissue (90). As shown in FIG. 5C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 6:
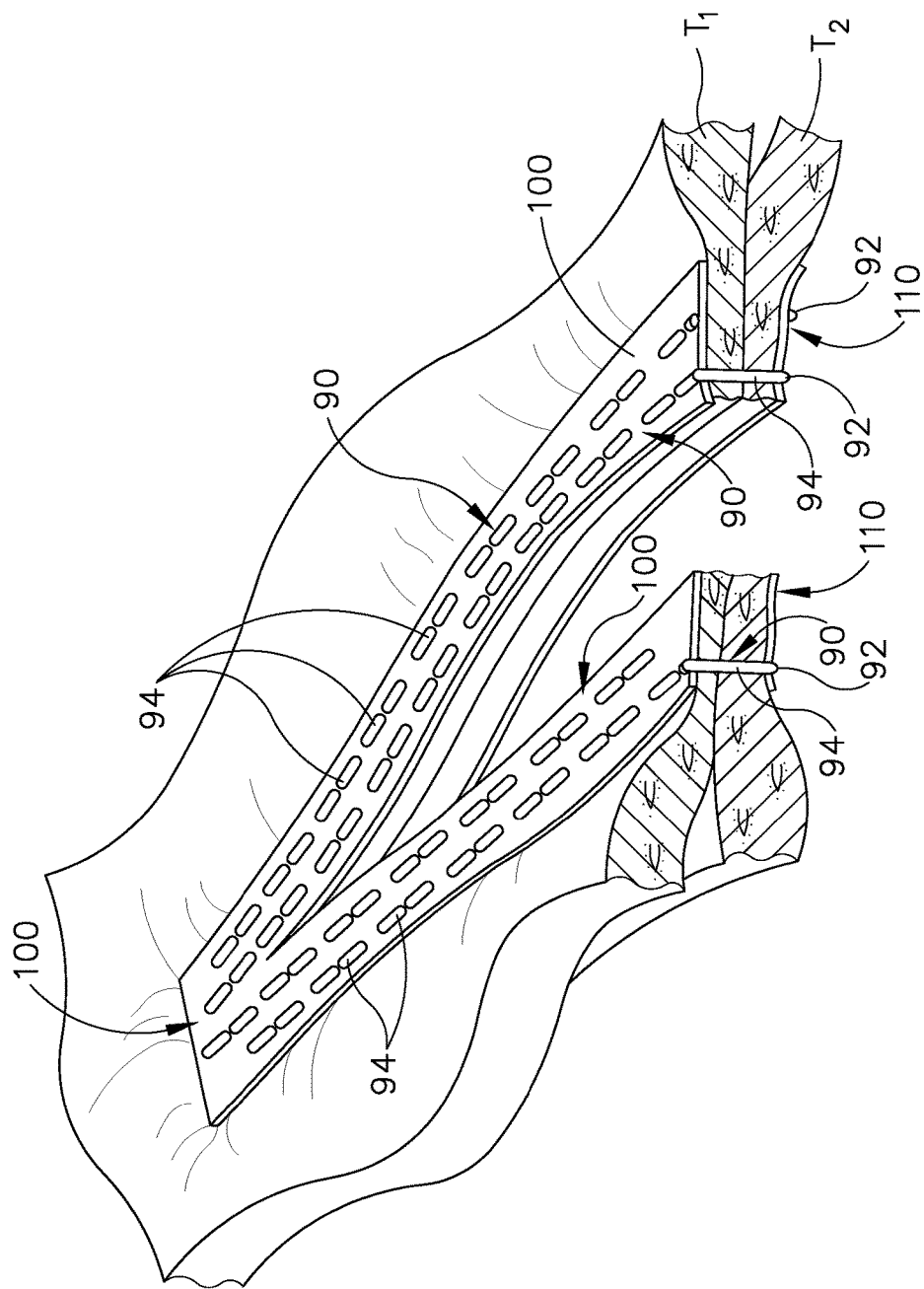
FIG. 6 depicts a perspective view of staples and the buttress assembly of FIG. 5A having been secured to the tissue by the end effector of FIG. 2.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 6. As end effector (40) is pulled away from tissue (90) after deploying staples (90) and buttress assemblies (100, 110), buttress assemblies (100, 110) disengage end effector), such that buttress assemblies (100, 110) remain secured to tissue ($T_1$, $T_2$) with staples (90). Buttress tissue ($T_1$, $T_2$) thus provide structural reinforcement to the lines of staples (90). As can also be seen in FIG. 6, knife member (80) also cuts through a centerline of buttress tissue assemblies (100, 110), separating each buttress assemblies (100, 110) into a corresponding pair of sections, such that each section remains secured to a respective severed region of tissue ($T_1$, $T_2$).

In the foregoing example, buttress assembly (100) is sized to span across the full width of underside (65), such that buttress assembly (100) spans across channel (62). Thus, knife member (80) cuts through buttress assembly (100) during actuation of end effector (40) as described above. In some other examples, such as those described below, buttress assembly (100) is provided in two separate, laterally spaced apart portions, with one portion being disposed on underside (65) on one side of channel (62) and another portion being disposed on underside (65) on the other side of channel (62). In such versions, buttress assembly (100) does not span across channel (62), such that knife member (80) does not cut through buttress assembly (100) during actuation of end effector (40).

Likewise, buttress assembly (110) may be sized to span across the full width of deck (73), such that buttress assembly (110) spans across channel (72), and such that knife member (80) cuts through buttress assembly (110) during actuation of end effector (40) as described above. Alternatively, buttress assembly (110) may be provided in two separate, laterally spaced apart portions, with one portion being disposed on deck (73) on one side of channel (72) and another portion being disposed on deck (73) on the other side of channel (72), such that buttress assembly (110) does not span across channel (72), and such that knife member (80) does not cut through buttress assembly (110) during actuation of end effector (40).

III. Exemplary Humidity Tolerant Adhesive Materials and Techniques for Providing Adhesion of Buttress to Moist Surgical Stapler and/or Moist Tissue In some surgical applications, it may be desirable to provide a buttress body (102, 112) with one or more adhesive materials (104, 114) that will maintain adhesive properties in a humid (i.e., moist or wet) environment, when buttress body (102, 112) is used intraoperatively, for a sufficient amount of time to complete the surgical procedure. Such humidity tolerant adhesive materials may provide for temporary attachment of a buttress body (102, 112) to a wet jaw (50) or wet anvil (60) of the end effector (40) of a surgical stapling instrument (10), serve as an adjunct to reinforce the mechanical fastening of moist tissue ($T_1$, $T_2$) that is provided by staples (90), and combinations thereof. Such humidity tolerant adhesives may ultimately degrade and be absorbed by the body.

In some instances, the one or more adhesive materials (104, 114) have a humidity tolerance that is defined as the ability to maintain the temporary attachment of a buttress body (102, 112) to a jaw (50) or anvil (60) of an end effector (40) for at least ten minutes in an environment having 100% humidity (e.g., inside a patient) after buttress assembly (100, 110) has previously been exposed to a relative humidity of from 20% to 60% for a period up to sixty minutes at a temperature of from about 15° C. to about 25° C.

Figure 7:
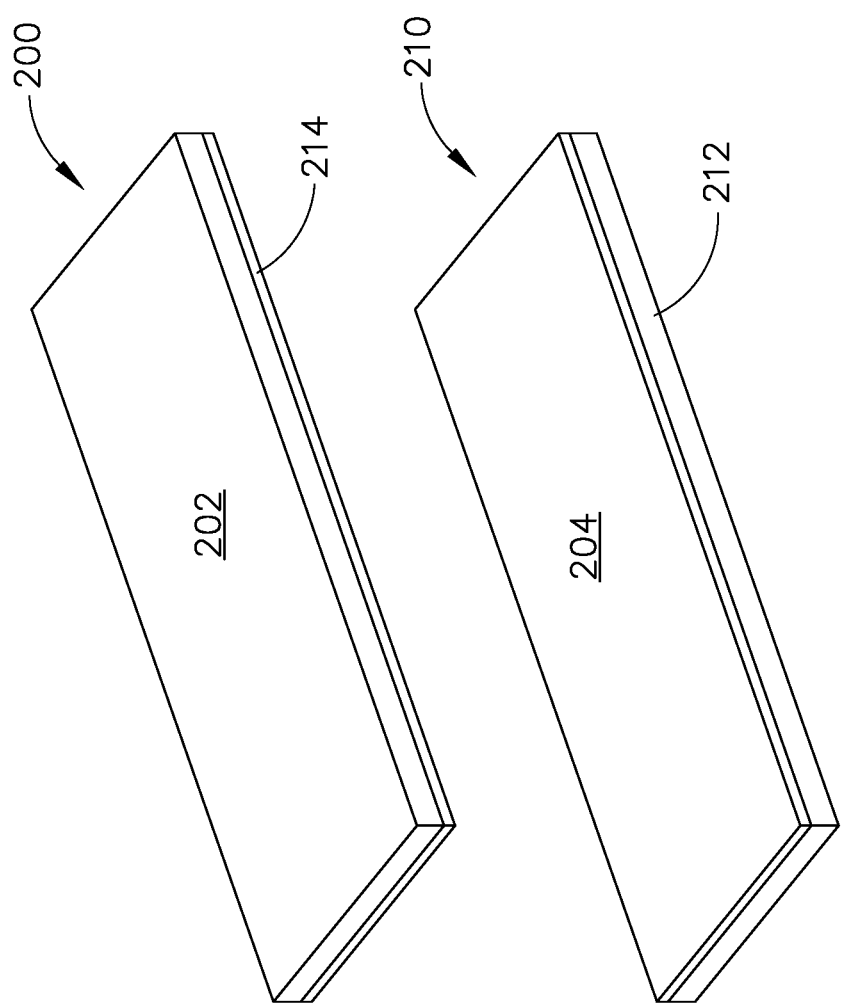
FIG. 7 depicts a perspective view of another exemplary upper buttress and an another exemplary lower buttress, each of which may be applied to the end effector of FIG. 2.
Figure 8:
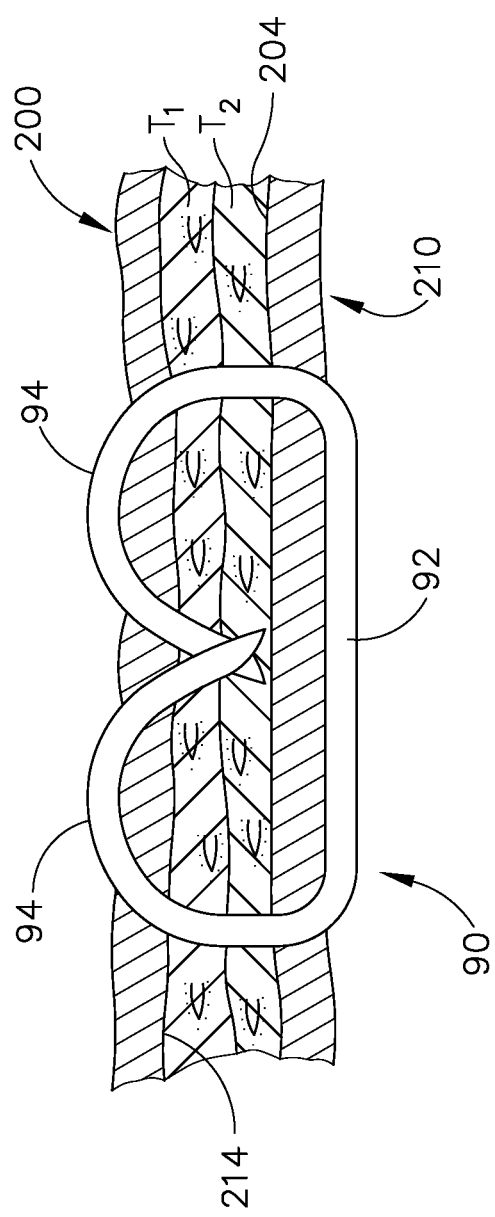
FIG. 8 depicts a cross-sectional view of a staple and the upper and lower buttresses of FIG. 7 having been secured to the tissue by the end effector of FIG. 2.

By way of example, FIG. 7 shows an exemplary buttress assembly (200) that may be used in place of buttress assembly (100) described above. Buttress assembly (200) of this example comprises an upper buttress body (202) with a lower adhesive layer (214). Buttress assembly (200) of this example further comprises a lower buttress body (212) with an upper adhesive layer (204). In use, the lower and upper adhesive layers (214, 204) temporarily adhere to wet tissue ($T_1$, $T_2$) to serve as an adjunct to reinforce the mechanical fastening of the tissue provided by staples (90) as shown in FIG. 8. Of course, the applied staples (90) will also secure buttress assembly (200) to tissue ($T_1$, $T_2$). Before buttress assembly (200) is applied to tissue ($T_1$, $T_2$), buttress assembly (200) may be removably secured to end effector (40) in any suitable fashion as will be apparent to those of ordinary skill in the art in view of the teachings herein.

Figure 9:
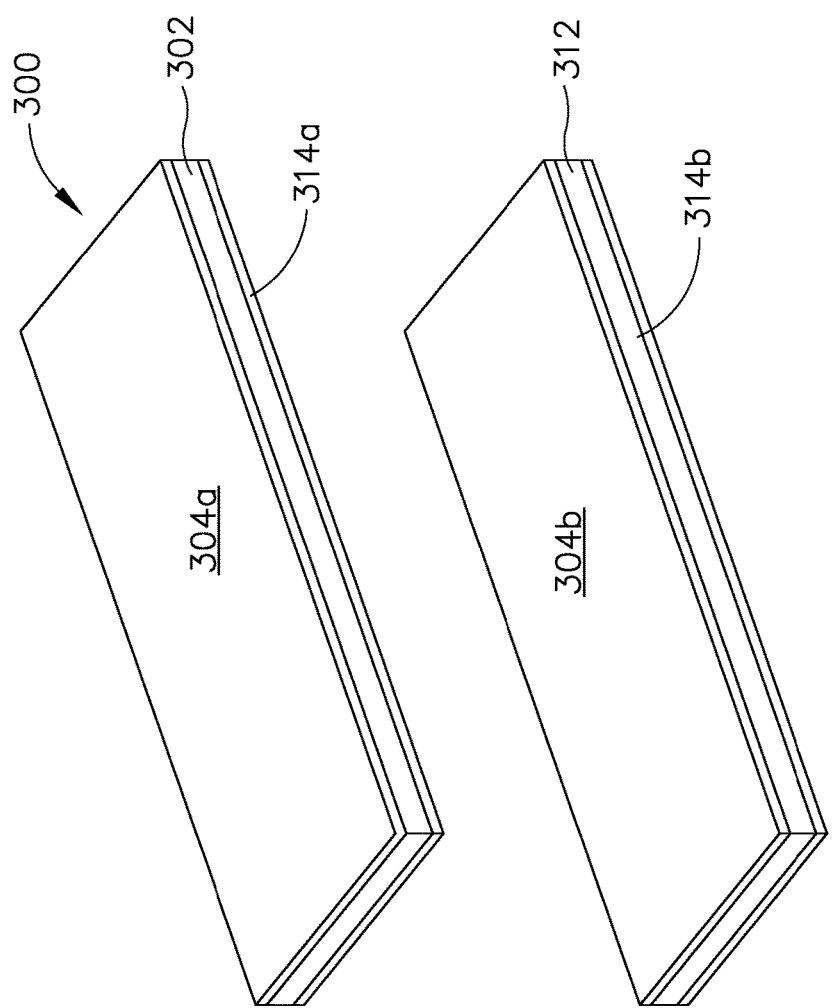
FIG. 9 depicts a perspective view of another exemplary upper buttress and another exemplary lower buttress, each of which may be applied to the end effector of FIG. 2.

FIG. 9 shows another exemplary buttress assembly (300) that may be used in place of buttress assembly (100) described above. Buttress assembly (300) of this example comprises an upper buttress body (302) that has an upper adhesive layer (304a) and a lower adhesive layer (314a). Buttress assembly (300) further comprises a lower buttress body (312) having an upper adhesive layer (304b) and a lower adhesive layer (314b). In use, upper and lower adhesive layers (304a, 314b) respectively provide for temporary attachment of the buttress bodies (302, 312) to underside (65) of anvil (60) and deck (73) of staple cartridge (70). Lower and upper adhesive layers (314a, 304b) temporarily adhere to tissue ($T_1$, $T_2$) to serve as an adjunct to reinforce the mechanical fastening of wet tissue provided by staples (90). Of course, the applied staples (90) will also secure buttress assembly (300) to tissue ($T_1$, $T_2$).

In some instances, the humidity tolerant adhesive materials (e.g., one or more of layers (104, 204, 304, 114, 214, 314)) for a buttress body (102, 202, 302, 112, 212, 312) comprise bioabsorbable polymers. Various physiomechanical properties of polymers may be modified in order to provide different adhesive properties. Such variable characteristics include but are not limited to copolymer composition, polymer architecture (e.g., random vs. block copolymers and/or branching), glass transition temperature (Tg), molecular weight (number average or weight average), inherent viscosity (IV), crystallinity, sequence distribution, copolymer chain composition, melting temperature (Tm), surface tension and rheological properties. Several exemplary combinations of these variables will be provided below, though it should be understood that these examples are merely illustrative. It should also be understood that these examples of adhesive materials may be provided in upper adhesive layer (104, 204, 304). In addition or in the alternative, these examples of adhesive materials may be provided in lower adhesive layer (114, 214, 314). In addition or in the alternative, these examples of adhesive materials may be otherwise integrated into buttress body (102, 202, 302, 112, 212, 312). It should therefore be understood that the adhesive material need not necessarily constitute a separate layer that is discretely identifiable as being different from a layer defined by buttress body (102, 202, 302, 112, 212, 312).

One of the aforementioned physiomechanical properties of polymers is glass transition temperature (Tg). Glass transition temperature (Tg) is the temperature at which the mechanical properties of a copolymer change dramatically from a flowable adhesive to a brittle plastic. It may thus be of importance that the glass transition temperature (Tg) is sufficiently below the operating temperature of the adhesive in order to allow for polymer chain mobility. The glass transition temperature (Tg) is lower than the melting point of the crystalline form of the same copolymer. The glass transition temperature (Tg) may be indicative of how the polymer behaves under ambient conditions. The glass transition temperature (Tg) can be effected by composition, polymer chain configuration and stiffness, molecular weight, viscosity, shear modulus, heat capacity, thermal expansion, cross-linking and other factors. It is therefore possible to have a relatively low glass transition temperature (Tg) material composition that does not always correspond to low molecular weight or low inherent viscosity (IV).

The melting temperature of a polymer may be referred to as the "first-order transition," which is where the polymer changes from a solid to liquid. Crystalline polymers have a true melting point, which is the temperature at which the crystallites melt and the total mass of plastic becomes amorphous. Amorphous polymers do not have a true melting point, but they do have a first-order transition wherein their mechanical behavior transitions from a rubbery nature to viscous rubbery flow. Suitable polymers for use in forming adhesive layers (104, 204, 304, 114, 214, 314) may have a percentage of crystallinity making them semi-crystalline, thus having both amorphous and crystalline domains. The melting point of the polymer may be sufficiently high above the operating temperature of the adhesive to maintain cohesive strength and provide dimensional stability of the applied adhesive.

Inherent viscosity (IV) reflects a measurement of molecular size. It is based on the flow time of a polymer solution through small capillary channels over time. The inherent viscosity (IV) and molecular weight of a polymer are related, but that relational agreement is different for each copolymer composition. For instance, the correlation of inherent viscosity (IV) to molecular weight may be logarithmic with only a small midsection of the curve being linear. This logarithmic correlation may differ as the copolymer composition differs. It is not necessarily required to have a low molecular weight copolymer in order to manifest adhesive and malleable properties. Low molecular weight copolymers may also have shortened degradation cycles and reduced structural strength. The ideal adhesion film or adhesive substrate to use in adhesive layers (104, 204, 304, 114, 214, 314) may have higher molecular weight and low inherent viscosity (IV) to be both strong and adhesive. This may be achieved, for example, by the introduction of polymer branching. The molecular weight of the adhesive may need to be high enough to provide mechanical strength to the adhesive to avoid cohesive failure, but also sufficiently low enough that it can be cleared from the body through degradation in an acceptable amount of time.

Further important properties of the polymers include their surface tension and rheological properties. If there is a sufficiently large mismatch between the surface tension of the adhesive and the surfaces to be adhered to, adhesion may be energetically unfavorable. Similarly, the rheological properties of the polymer such as bulk moduli may need to be such that the polymer can flow to conform to the surface topography of deck (73) or underside (65), while simultaneously providing enough integrity to maintain cohesive strength and to resist shearing off and/or peeling off of end effector (40).

In some instances, the humidity tolerant adhesive materials may be malleable. Malleable humidity tolerant adhesives may be highly viscous yet flowable at room temperature. A malleable humidity tolerant adhesive may, in response to pressure being applied to it, take the form of a surface with which it is engaged. In other words, if a malleable humidity tolerant adhesive is pressed against deck (73) of staple cartridge (70), the adhesive may take the form of the one or more features of the deck (73) that it the adhesive is pressed against. Similarly, if a malleable humidity tolerant polymer adhesive is pressed against underside (65) of anvil (60), the adhesive may take the form of the one or more features of underside (65) that the adhesive is pressed against. By deforming to the geometry that it is pressed against, the malleable humidity tolerant adhesive may adhere to the geometry, and may further provide re-applicable attachment. If the desired positioning of buttress assembly (100, 110) on deck (73) or underside (65) is not achieved, the malleable humidity tolerant adhesive may permit buttress assembly (100, 110) to be removed, repositioned, and re-adhered to deck (73) or underside (65). It should be understood that the humidity tolerant adhesives may be malleable at room temperature, such that additional heating or other treatment is not necessary in order to provide malleability.

Providing the humidity tolerant adhesive material in the form of a malleable polymer may minimize the impact of fluids and debris on the adhesion of buttress assembly (100, 110) to deck (73) of staple cartridge (70) or underside (65) of anvil (60). The malleable humidity tolerant adhesive material may also be hydrophilic (e.g., at least in certain regions of buttress assembly (100, 110)), encouraging adhesion in a wet environment. In addition or in the alternative, adhesive layer (104, 114) of buttress assembly (100) may include a combination of adhesive material and hydrophobic material in respective localized regions. The hydrophobic material may drive fluids out of the adhesion areas, thereby improving adhesion at the localized regions of adhesive material. In some examples, the humidity tolerant adhesive material may be combined with a buttress body (102,112) as disclosed in U.S. patent application Ser. No. 14/667,842, entitled "Method of Applying a Buttress to a Surgical Stapler," filed Mar. 25, 2015, the disclosure of which is incorporated by reference herein.

In some instances, the humidity tolerant adhesive materials may be extrudable. The extrudable adhesive may be extruded through a die that may be positioned directly next to or adjacent to the extruder. A melt pump may be used between the die and extruder. The die may be used to form an extrudate that is generally planar and continuous or to form discrete deposits (e.g., rod-shaped deposits) on the surface of a buttress assembly (100, 110) before it is pressed against a deck (73) of staple cartridge (70) or pressed against the underside of an anvil (60).

A. Exemplary Humidity Tolerant Adhesives with A-B-A Block Polymer Configurations In some instances, the humidity tolerant adhesive materials (e.g., one or more of layers (104, 204, 304, 114, 214, 314)) for a buttress body (102, 202, 302, 112, 212, 312) comprise polymers having a general A-B-A block configuration. In illustrative examples, the A-B-A block polymers comprise by the percentage of their molecular weight: from about 1% to about 50%, or more particularly from about 5% to about 30% of A polymer blocks; and from about 50% to about 99%, or more particularly from about 70% to about 95%, of B polymer blocks.

The A polymer blocks are biodegradable, bioabsorbable, highly crystalline segments, which are homopolymers that may be characterized by a relatively high glass transition temperature (Tg) and/or a relatively high crystallinity. In illustrative examples, the A homopolymers may be characterized by a glass transition temperature (Tg) of at least about 0° C., preferably at least about 21° C. (i.e., room temperature). In addition, or in the alternative, the A homopolymers may be characterized by a crystallinity as measured by X-ray diffraction of at least about 30%, preferably at least about 40%, or more preferably at least about 45%. In addition, or in the alternative, the A homopolymers may have a molecular weight of at least about 5 kDa. Such exemplary A homopolymers may further be characterized by a melting temperature (Tm) of at least about 50° C., preferably at least about 60° C., and more preferably at least about 70° C.

Exemplary A homopolymers may be selected from the group of: poly(L-lactide) (PLLA); poly(caprolactone) (PCL); polyglycolide (PGA); poly(3-hydroxybutyrate) (PH$_3$B); poly(3-hydroxyvalerate) (PHV); and poly(p-dioxanone) (PPDO). It may be difficult to synthesize 100% A homopolymers. In some instances, the A homopolymers may contain a small percentage of residual B monomers. For example, exemplary A homopolymers may contain a small percentage (e.g., up to about 10% by weight) of B monomers.

The B polymer blocks are biodegradable, bioabsorbable homopolymers or co-polymers, which are predominantly amorphous and may be characterized by a relatively low to moderate glass transition temperature (Tg). In illustrative examples, the B polymers as homopolymers or co-polymers may be characterized by glass transition temperature (Tg) of at least about −40° C., more particularly at least about −30° C., and more particularly at least about −20° C. In addition, or in the alternative, the B homopolymers or co-polymers may be characterized by a crystallinity as measured by X-ray diffraction of at most about 25%, more particularly at most about 10%, or more particularly at most about 5%. In addition, or in the alternative, the B polymers as homopolymers or co-polymers may have a molecular weight of from about 20 to about 80 kDa, more particularly from about 30 to about 70 kDa, and more particularly, from about 40 to about 65 kDa.

Exemplary B homopolymers or co-polymers comprise monomers selected from the group consisting of: caprolactone (CL), L-Lactide (LLA), D,L-Lactide ((D,L)LA), Glycolide (GA), Polydioxanone (PDO), Trimethylene carbonate (TMC), sebacic acid (SA), 1,6-bis(carboxyphenoxy)hexane (CPH), and combinations thereof.

In some instances, the humidity tolerant adhesive materials having a general A-B-A block configuration may be blended with a tackifying agent to provide for an extrudable adhesive. Such extrudable humidity tolerant adhesive materials may be manufactured using hot melt extrusion. In illustrative examples, the A-B-A block polymer may be fed into a hot melt compounding twin-screw extruder. Once the A-B-A block polymer is sufficiently masticated and melted, the tackifying agent is added into the extruder. In some versions, additional compounds may be added in one or more additional steps to the extruder. Such additional compounds may selected from the group consisting of: plasticizing molecules; preservatives (e.g. antioxidants); fillers; and combinations thereof. Once mixing in the extruder is completed, the resulting adhesive may be fed through an extruder die and produced as a stand-alone flexible film that is then applied to a buttress body (102, 112). In addition, or in the alternative, the resulting adhesive may be fed through an extruder die and deposited directly onto a buttress body (102, 112). In any case, the adhesive may then be annealed to obtain any necessary phase separation at, near or above the A-block melting temperature, $T_m$. In addition, or in the alternative, the resulting adhesive may be sterilized, such as by treating it with ethylene oxide at a high temperature.

In illustrative examples, the tackifying agent may comprise a substantially amorphous biodegradable, bioabsorbable polymer with a molecular weight below the entanglement molecular weight. In addition, or alternative, the tackifying agent may have a glass transition above about 0° C., more particularly above about 20° C. In some examples, the tackifying agent may comprise a random copolymer of poly(L-lactide)-co-polyglycolide (PLGA) having a molecular weight of from about 1 to about 8 kDA, more particularly from about 1.5 to about 5 kDa.

In illustrative examples, an extrudable hot melt adhesive comprises ratios of polymer A-B-A and tackifying agent such that the glass transition of the blend ranges from about −5° C. to about 15° C., more particularly from 0° C. to about 10° C. In addition, or in the alternative, the rheological properties of the polymer such as bulk moduli need to be such that the polymer can flow to conform to the surface topography of deck (73) or underside (65), while at the same time, providing enough integrity to maintain cohesive strength and resisting shearing off and/or peeling off of end effector (40).

B. Exemplary Humidity Tolerant Adhesives with A-B-C Block Terpolymer Configurations In some instances, the humidity tolerant adhesive materials (e.g., one or more of layers (104, 204, 304, 114, 214, 314)) for a buttress body (102, 202, 302, 112, 212, 312) comprise polymers having a general A-B-C block terpolymer configuration, in which the C polymer block comprises a hydrophilic polymer. Generally it is theorized, but in no way limits the scope of this invention, that humidity tolerant adhesives comprising hydrophilic polymers may have better wet surface retention characteristics than adhesives comprising only hydrophobic polymers.

In some versions, the A-B-C block terpolymers may be combined with a water sorbent. Useful water sorbents may be selected from the group consisting of: carboxymethyl cellulose (CMC); polyvinylpyrrolidine (PVP); gelatin; hyaluronan; and combinations thereof. In some such examples, the A-B-C block terpolymers may be combined with water sorbent such that the resulting mixture comprises by its weight percentage from about 1% to about 60%, preferably from about 20% to about 40%, of the water sorbent.

The A polymer blocks are biodegradable, bioabsorbable, non-elastic, highly crystalline segments, which are homopolymers that may be characterized by a relatively high glass transition temperature (Tg) and/or a relatively high crystallinity. In illustrative examples, the A homopolymers may be characterized by a glass transition temperature (Tg) of at least about 0° C., more particularly at least about 21° C. (i.e., room temperature). In addition, or in the alternative, the A homopolymers may be characterized by a crystallinity as measured by X-ray diffraction of at least about 30%, more particularly at least about 40%, or more particularly at least about 45%. In addition, or in the alternative, the A homopolymers may have a molecular weight of at least about 5 kDa. Such exemplary A homopolymers may further be characterized by a melting temperature (Tm) of at least about 50° C., more particularly at least about 60° C., and more particularly at least about 70° C.

Exemplary A homopolymers may be selected from the group of: poly(L-lactide) (PLLA); poly(caprolactone) (PCL); polyglycolide (PGA); poly(3-hydroxybutyrate) (PH$_3$B); poly(3-hydroxyvalerate) (PHV); and poly(p-dioxanone) (PPDO). It may be difficult to synthesize 100% A homopolymers. The A homopolymers may thus contain a small percentage of residual B monomers. For example, exemplary A homopolymers may contain a small percentage (e.g., up to about 10% by weight) of B monomers.

The B polymer blocks are biodegradable, bioabsorbable, elastomeric homopolymers or co-polymers, which are predominantly amorphous and may be characterized by a relatively low to moderate glass transition temperature (Tg). In illustrative examples, the B polymers as homopolymers or co-polymers may be characterized by glass transition temperature (Tg) of at least about −40° C., more particularly at least about −30° C., and more particularly at least about −20° C. In addition, or in the alternative, the B homopolymers or co-polymers may be characterized by a crystallinity as measured by X-ray diffraction of at most about 25%, more particularly at most about 10%, or more particularly at most about 5%. In addition, or in the alternative, the B polymers as homopolymers or co-polymers may have a molecular weight of from about 20 to about 80 kDa, more particularly from about 30 to about 70 kDa, and more particularly, from about 40 to about 65 kDa. In addition, or in the alternative, the B polymers as homopolymers may have a an entanglement molecular weight of from about 3 to 4 kDa.

Exemplary B homopolymers or co-polymers comprise monomers selected from the group consisting of: caprolactone (CL), L-Lactide (LLA), D,L-Lactide ((D,L)LA), Glycolide (GA), Polydioxanone (PDO), Trimethylene carbonate (TMC), sebacic acid (SA), 1,6-bis(carboxyphenoxy)hexane (CPH), and combinations thereof. As another merely illustrative example, B polymers or co-polymers may be selected from the group of: caprolactone-co-glycolide (CAP-co-GLY); poly(L-lactide)-co-glycolide (PLGA); poly(D,L-lactide) (P(D,L)LA); poly(caprolactone)-co-glycolide (PCL-co-GA); poly[(1,6-bis(p-carboxyphenoxy)hexane)-co-sebacic acid (PCPH-co-SA); poly(trimethylene carbonate) (PTMC); poly(trimethylene carbonate)-co-glycolide (PTMC-co-GA; and poly(trimethylene carbonate)-co-caprolactone (PTMC-co-CL).

The C polymer blocks are biodegradable, bioabsorbable, hydrophilic homopolymers or co-polymers and may be characterized by miscibility with water at 37° C. Exemplary C homopolymers and co-polymers may be selected from the group of: polyethylene oxide (PEO); polyethylene oxide-co-polypropylene oxide (PEO-co-PPO); polyethylene oxide-co-polysulfone (PEO-co-PSO); polyvinylpyrrolidine (PVP); polyacrylic acid (PAA); and polyvinyl alcohol (PVOH).

In an illustrative example of a useful A-B-C block terpolymer, A is glycolide (GLY), B is a co-polymer of caprolactone-glycolide (CAP-co-GLY) and C is polyethylene oxide (PEO).

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, the disclosure of which is incorporated by reference herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A buttress assembly that is configured to temporarily adhere to a wet surgical stapler end effector, the buttress assembly comprising: (a) a buttress body; and (b) a humidity tolerant adhesive applied to at least one side of the buttress body, the humidity tolerant adhesive comprising a bioabsorbable polymer having a block configuration selected from the group consisting of: (i) A-B-A, and (ii) A-B-C, wherein the A block is a bioabsorbable homopolymer characterized by a glass transition temperature of at least about 0° C., a crystallinity as measured by X-ray diffraction of at least about 30%, and a melting temperature of at least about 50° C.; wherein the B block is a bioabsorbable homopolymer or co-polymer that is characterized by a glass transition temperature of at least about −40° C., a crystallinity as measured by X-ray diffraction of at most about 25%, and a molecular weight of from about 20 to about 80 kDa; and wherein the C block is a bioabsorbable hydrophilic homopolymer or co-polymer that is miscible with water at 37° C.

EXAMPLE 2

The buttress assembly of Example 1, wherein the A block is a homopolymer selected from the group consisting of: poly(L-lactide) (PLLA); poly(caprolactone) (PCL); polyglycolide (PGA); poly(3-hydroxybutyrate) ($PH_3B$); poly(3-hydroxyvalerate) (PHV); and poly(p-dioxanone) (PPDO).

EXAMPLE 3

The buttress assembly of any one or more of Examples 1 through 2, wherein the B block is a homopolymer or co-polymer comprising monomer(s) selected from the group consisting of: caprolactone (CL), L-Lactide (LLA), D,L-Lactide ((D,L)LA), Glycolide (GA), Polydioxanone (PDO), Trimethylene carbonate (TMC), sebacic acid (SA), 1,6-bis(carboxyphenoxy)hexane (CPH), and combinations thereof.

EXAMPLE 4

The buttress assembly of any one or more of Examples 1 through 3, wherein the C block is a hydrophilic homopolymer or co-polymer selected from the group consisting of: polyethylene oxide (PEO); polyethylene oxide-co-polypropylene oxide (PEO-co-PPO); polyethylene oxide-co-polysulfone (PEO-co-PSO); polyvinylpyrrolidine (PVP); polyacrylic acid (PAA); polyvinyl alcohol (PVOH).

EXAMPLE 5

The buttress assembly of any one or more of Examples 1 through 4, wherein the humidity tolerant adhesive comprises a bioabsorbable polymer having an A-B-A block configuration and a tackifying agent, wherein the humidity tolerant adhesive is extruded onto the at least one side of the buttress body.

EXAMPLE 6

The buttress assembly of Example 5, wherein the tackifying agent is a poly(L-lactide)-co-polyglycolide (PLGA) random heteropolymer having a molecular weight of from about 1 to about 8 kDA.

EXAMPLE 7

The buttress assembly of any one or more of Examples 1 through 6, wherein the humidity tolerant adhesive comprises a bioabsorbable polymer having an A-B-A block configuration and further comprising a tackifying agent, wherein the humidity tolerant adhesive is extruded to form a flexible film that is applied to at least one side of the buttress body.

EXAMPLE 8

The buttress assembly of any one or more of Examples 1 through 7, wherein the humidity tolerant adhesive comprises a bioabsorbable polymer having an A-B-C block configuration, wherein A is glycolide (GLY), B is a co-polymer of caprolactone-glycolide (CAP-co-GLY) and C is polyethylene oxide (PEO).

EXAMPLE 9

The buttress assembly of any one or more of Examples 1 through 8, wherein the buttress body comprises polyglactin 910.

EXAMPLE 10

The buttress assembly of Example 9, wherein the polyglactin 910 is in the form of a woven mesh.

EXAMPLE 11

A method of applying a buttress assembly to a wet surgical stapler end effector, wherein the end effector comprises an anvil and staple cartridge, the method comprising the steps of: (a) positioning the buttress assembly between the anvil and the staple cartridge, wherein the buttress assembly comprises a buttress body and a humidity tolerant adhesive material, wherein the humidity tolerant adhesive material comprises a bioabsorbable polymer having a block configuration selected from the group of: (i) A-B-A, and (ii) A-B-C, wherein the A block is a bioabsorbable homopolymer characterized by a glass transition temperature of at least about 0° C., and a crystallinity as measured by X-ray diffraction of at least about 30%, wherein the B block is a bioabsorbable homopolymer or co-polymer that is characterized by a glass transition temperature of at least about −40° C., a crystallinity as measured by X-ray diffraction of at most about 25%, and a molecular weight of from about 20 to about 80 kDa, wherein the C block is a bioabsorbable hydrophilic homopolymer or co-polymer that is miscible with water at 37° C., wherein the humidity tolerant adhesive material faces either an underside of the anvil or a deck of the staple cartridge, wherein the anvil is in an open position relative to the staple cartridge during the act of positioning the buttress assembly between the anvil and the staple cartridge; (b) moving the anvil toward the staple cartridge to press the humidity tolerant adhesive material against the anvil or the staple cartridge; and (c) moving the anvil back to the open position, wherein the buttress assembly is adhered to the anvil or the deck of the staple cartridge via the humidity tolerant adhesive material with the anvil moved back to the open position,

EXAMPLE 12

The method of Example 11, wherein the A block is a homopolymer selected from the group consisting of: poly (L-lactide) (PLLA); poly(caprolactone) (PCL); polyglycolide (PGA); poly(3-hydroxybutyrate) ($PH_3B$); poly(3-hydroxyvalerate) (PHV); and poly(p-dioxanone) (PPDO).

EXAMPLE 13

The method of any one or more of Examples 11 through 12, wherein the B block is a homopolymer or co-polymer comprising monomer(s) selected from the group consisting of: caprolactone (CL), L-Lactide (LLA), D,L-Lactide ((D,L)LA), Glycolide (GA), Polydioxanone (PDO), Trimethylene carbonate (TMC), sebacic acid (SA), 1,6-bis(carboxyphenoxy)hexane (CPH), and combinations thereof.

EXAMPLE 14

The method of any one or more of Examples 11 through 13, wherein the C block is a hydrophilic homopolymer or co-polymer selected from the group consisting of: polyethylene oxide (PEO); polyethylene oxide-co-polypropylene oxide (PEO-co-PPO); polyethylene oxide-co-polysulfone (PEO-co-PSO); polyvinylpyrrolidine (PVP); polyacrylic acid (PAA); polyvinyl alcohol (PVOH).

EXAMPLE 15

The method of any one or more of Examples 11 through 14, wherein the humidity tolerant adhesive comprises a bioabsorbable polymer having an A-B-A block configuration and further comprising a tackifying agent, wherein the humidity tolerant adhesive is extruded onto the at least one side of the buttress body.

EXAMPLE 16

The method of Example 15, wherein the tackifying agent is a poly(L-lactide)-co-polyglycolide (PLGA) random heteropolymer having a molecular weight of from about 1 to about 8 kDA.

EXAMPLE 17

The method of any one or more of Examples 11 through 16, wherein the humidity tolerant adhesive comprises a bioabsorbable polymer having an A-B-A block configuration and further comprising a tackifying agent, wherein the humidity tolerant adhesive is extruded to form a flexible film that is applied to at least one side of the buttress body.

EXAMPLE 18

The method of Example 17, wherein the tackifying agent is a poly(L-lactide)-co-glycolide (PLGA) random heteropolymer having a molecular weight of from about 1 to about 8 kDA.

EXAMPLE 19

The method of any one or more of Examples 11 through 18, further comprising: (a) removing the buttress assembly from the wet surgical stapler end effector; and (b) re-applying the buttress assembly to the wet surgical stapler end effector.

EXAMPLE 20

A buttress assembly that is configured to temporarily adhere to a wet surgical stapler end effector, the buttress assembly comprising: (a) a buttress body; and (b) a humidity tolerant adhesive applied to at least one side of the buttress body, the humidity tolerant adhesive comprising a bioabsorbable polymer having a block configuration selected from the group of: (i) A-B-A, and (iii) A-B-C, wherein the A block is bioabsorbable homopolymer selected from the group consisting of: poly(L-lactide) (PLLA); poly(caprolactone) (PCL); polyglycolide (PGA); poly(3-hydroxybutyrate) (PH$_3$B); poly(3-hydroxyvalerate) (PHV); and poly(p-dioxanone) (PPDO), wherein the B block is a homopolymer or co-polymer comprising monomer(s) selected from the group consisting of: caprolactone (CL), L-Lactide (LLA), D,L-Lactide ((D,L)LA), Glycolide (GA), Polydioxanone (PDO), Trimethylene carbonate (TMC), sebacic acid (SA), 1,6-bis(carboxyphenoxy)hexane (CPH), and combinations thereof, and wherein the C block is a hydrophilic homopolymer or co-polymer selected from the group consisting of: polyethylene oxide (PEO); polyethylene oxide-co-polypropylene oxide (PEO-co-PPO); polyethylene oxide-co-polysulfone (PEO-co-PSO); polyvinylpyrrolidine (PVP); polyacrylic acid (PAA); polyvinyl alcohol (PVOH).

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, the disclosure of which is incorporated by reference herein; U.S. patent application Ser. No. 14/827,856, entitled "Implantable Layers for a Surgical Instrument," filed Aug. 17, 2015, the disclosure of which is incorporated by reference herein; U.S. patent application Ser. No. 14/871,071, entitled "Compressible Adjunct with Crossing Spacer Fibers," filed Sep. 30, 2015, the disclosure of which is incorporated by reference herein; and U.S. patent application Ser. No. 14/871,131, entitled "Method for Applying an Implantable Layer to a Fastener Cartridge," filed Sep. 30, 2015, the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein; and/or U.S. patent application Ser. No. 14/871,131, entitled "Method for Applying an Implantable Layer to a Fastener Cartridge," filed Sep. 30, 2015, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, the disclosure of which is incorporated by reference herein; U.S. Pub. No. 2012/0199630, entitled "Robotically-Controlled Surgical Instrument with Force-Feedback Capabilities," published Aug. 9, 2012, the disclosure of which is incorporated by reference herein; U.S. Pub. No. 2012/0132450, entitled "Shiftable Drive Interface for Robotically-Controlled Surgical Tool," published May 31, 2012, the disclosure of which is incorporated by reference herein; U.S. Pub. No. 2012/0199633, entitled "Surgical Stapling Instruments with Cam-Driven Staple Deployment Arrangements," published Aug. 9, 2012, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, the disclosure of which is incorporated by reference herein; U.S. Pub. No. 2012/0199632, entitled "Robotically-Controlled Surgical Instrument with Selectively Articulatable End Effector," published Aug. 9, 2012, the disclosure of which is incorporated by reference herein; U.S. Pub. No. 2012/0203247, entitled "Robotically-Controlled Surgical End Effector System," published Aug. 9, 2012, the disclosure of which is incorporated by reference herein; U.S. Pub. No. 2012/0211546, entitled "Drive Interface for Operably Coupling a Manipulatable Surgical Tool to a Robot," published Aug. 23, 2012; U.S. Pub. No. 2012/0138660, entitled "Robotically-Controlled Cable-Based Surgical End Effectors," published Jun. 7, 2012, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A buttress assembly that is configured to temporarily adhere to a wet surgical stapler end effector, the buttress assembly comprising:
   (a) a buttress body; and
   (b) a humidity tolerant adhesive applied to at least one side of the buttress body, the humidity tolerant adhesive comprising a bioabsorbable polymer having a block configuration selected from the group consisting of:

(i) A-B-A, and
(ii) A-B-C,
wherein the A block is a bioabsorbable homopolymer characterized by a glass transition temperature of at least about 0° C., a crystallinity as measured by X-ray diffraction of at least about 30%, and a melting temperature of at least about 50° C.;
wherein the B block is a bioabsorbable homopolymer or co-polymer that is characterized by a glass transition temperature of at least about −40° C., a crystallinity as measured by X-ray diffraction of at most about 25%, and a molecular weight of from about 20 to about 80 kDa; and
wherein the C block is a bioabsorbable hydrophilic homopolymer or co-polymer that is miscible with water at 37° C.

2. The buttress assembly according to claim 1, wherein the A block is a homopolymer selected from the group consisting of: poly(L-lactide) (PLLA); poly(caprolactone) (PCL); polyglycolide (PGA); poly(3-hydroxybutyrate) (PH$_3$B); poly(3-hydroxyvalerate) (PHV); and poly(p-dioxanone) (PPDO).

3. The buttress assembly according to claim 1, wherein the B block is a homopolymer or co-polymer comprising monomer(s) selected from the group consisting of: caprolactone (CL), L-Lactide (LLA), D,L-Lactide ((D,L)LA), Glycolide (GA), Polydioxanone (PDO), Trimethylene carbonate (TMC), sebacic acid (SA), 1,6-bis(carboxyphenoxy)hexane (CPH), and combinations thereof.

4. The buttress assembly according to claim 1, wherein the C block is a hydrophilic homopolymer or co-polymer selected from the group consisting of: polyethylene oxide (PEO); polyethylene oxide-co-polypropylene oxide (PEO-co-PPO); polyethylene oxide-co-polysulfone (PEO-co-PSO); polyvinylpyrrolidine (PVP); polyacrylic acid (PAA); polyvinyl alcohol (PVOH).

5. The buttress assembly according to claim 1, wherein the humidity tolerant adhesive comprises a bioabsorbable polymer having an A-B-A block configuration and a tackifying agent, wherein the humidity tolerant adhesive is extruded onto the at least one side of the buttress body.

6. The buttress assembly according to claim 5, wherein the tackifying agent is a poly(L-lactide)-co-polyglycolide (PLGA) random heteropolymer having a molecular weight of from about 1 to about 8 kDA.

7. The buttress assembly according to claim 1, wherein the humidity tolerant adhesive comprises a bioabsorbable polymer having an A-B-A block configuration and further comprising a tackifying agent, wherein the humidity tolerant adhesive is extruded to form a flexible film that is applied to at least one side of the buttress body.

8. The buttress assembly according to claim 1, wherein the humidity tolerant adhesive comprises a bioabsorbable polymer having an A-B-C block configuration, wherein A is glycolide (GLY), B is a co-polymer of caprolactone-glycolide (CAP-co-GLY) and C is polyethylene oxide (PEO).

9. The buttress assembly according to claim 1, wherein the buttress body comprises polyglactin 910.

10. The buttress assembly according to claim 9, wherein the polyglactin 910 is in the form of a woven mesh.

11. A method of applying a buttress assembly to a wet surgical stapler end effector, wherein the end effector comprises an anvil and staple cartridge, the method comprising the steps of:
(a) positioning the buttress assembly between the anvil and the staple cartridge, wherein the buttress assembly comprises a buttress body and a humidity tolerant adhesive material, wherein the humidity tolerant adhesive material comprises a bioabsorbable polymer having a block configuration selected from the group of:
(i) A-B-A, and
(ii) A-B-C,
wherein the A block is a bioabsorbable homopolymer characterized by a glass transition temperature of at least about 0° C., and a crystallinity as measured by X-ray diffraction of at least about 30%,
wherein the B block is a bioabsorbable homopolymer or co-polymer that is characterized by a glass transition temperature of at least about −40° C., a crystallinity as measured by X-ray diffraction of at most about 25%, and a molecular weight of from about 20 to about 80 kDa,
wherein the C block is a bioabsorbable hydrophilic homopolymer or co-polymer that is miscible with water at 37° C.,
wherein the humidity tolerant adhesive material faces either an underside of the anvil or a deck of the staple cartridge, wherein the anvil is in an open position relative to the staple cartridge during the act of positioning the buttress assembly between the anvil and the staple cartridge;
(b) moving the anvil toward the staple cartridge to press the humidity tolerant adhesive material against the anvil or the staple cartridge; and
(c) moving the anvil back to the open position, wherein the buttress assembly is adhered to the anvil or the deck of the staple cartridge via the humidity tolerant adhesive material with the anvil moved back to the open position.

12. The method according to claim 11, wherein the A block is a homopolymer selected from the group consisting of: poly(L-lactide) (PLLA); poly(caprolactone) (PCL); polyglycolide (PGA); poly(3-hydroxybutyrate) (PH$_3$B); poly(3-hydroxyvalerate) (PHV); and poly(p-dioxanone) (PPDO).

13. The method according to claim 11, wherein the B block is a homopolymer or co-polymer comprising monomer(s) selected from the group consisting of: caprolactone (CL), L-Lactide (LLA), D,L-Lactide ((D,L)LA), Glycolide (GA), Polydioxanone (PDO), Trimethylene carbonate (TMC), sebacic acid (SA), 1,6-bis(carboxyphenoxy)hexane (CPH), and combinations thereof.

14. The method according to claim 11, wherein the C block is a hydrophilic homopolymer or co-polymer selected from the group consisting of: polyethylene oxide (PEO); polyethylene oxide-co-polypropylene oxide (PEO-co-PPO); polyethylene oxide-co-polysulfone (PEO-co-PSO); polyvinylpyrrolidine (PVP); polyacrylic acid (PAA); polyvinyl alcohol (PVOH).

15. The method according to claim 11, wherein the humidity tolerant adhesive comprises a bioabsorbable polymer having an A-B-A block configuration and further comprising a tackifying agent, wherein the humidity tolerant adhesive is extruded onto the at least one side of the buttress body.

16. The method according to claim 15, wherein the tackifying agent is a poly(L-lactide)-co-polyglycolide (PLGA) random heteropolymer having a molecular weight of from about 1 to about 8 kDA.

17. The method according to claim 15, wherein the tackifying agent is a poly(L-lactide)-co-polyglycolide (PLGA) random heteropolymer having a molecular weight of from about 1 to about 8 kDA.

18. The method according to claim 11, wherein the humidity tolerant adhesive comprises a bioabsorbable polymer having an A-B-A block configuration and further comprising a tackifying agent, wherein the humidity tolerant adhesive is extruded to form a flexible film that is applied to at least one side of the buttress body.

19. The method according to claim 11, further comprising:
 (a) removing the buttress assembly from the wet surgical stapler end effector; and
 (b) re-applying the buttress assembly to the wet surgical stapler end effector.

20. A buttress assembly that is configured to temporarily adhere to a wet surgical stapler end effector, the buttress assembly comprising:
 (a) a buttress body; and
 (b) a humidity tolerant adhesive applied to at least one side of the buttress body, the humidity tolerant adhesive comprising a bioabsorbable polymer having a block configuration selected from the group of:
  (i) A-B-A, and
  (iii) A-B-C, wherein the A block is bioabsorbable homopolymer selected from the group consisting of: poly(L-lactide) (PLLA); poly(caprolactone) (PCL); polyglycolide (PGA); poly(3-hydroxybutyrate) ($PH_3B$); poly(3-hydroxyvalerate) (PHV); and poly(p-dioxanone) (PPDO), wherein the B block is a homopolymer or co-polymer comprising monomer(s) selected from the group consisting of: caprolactone (CL), L-Lactide (LLA), D,L-Lactide ((D,L)LA), Glycolide (GA), Polydioxanone (PDO), sebacic acid (SA), 1,6-bis(carboxyphenoxy)hexane (CPH), and combinations thereof, and wherein the C block is a hydrophilic homopolymer or co-polymer selected from the group consisting of: polyethylene oxide (PEO); polyethylene oxide-co-polypropylene oxide (PEO-co-PPO); polyethylene oxide-co-polysulfone (PEO-co-PSO); polyvinylpyrrolidine (PVP); polyacrylic acid (PAA); polyvinyl alcohol (PVOH).

* * * * *